US007217518B2

(12) United States Patent
Sekar et al.

(10) Patent No.: US 7,217,518 B2
(45) Date of Patent: May 15, 2007

(54) FLUORESCENCE POLARIZATION ASSAY

(75) Inventors: Michael M. A. Sekar, Santa Clara, CA (US); I. Lawrence Greenfield, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/628,879

(22) Filed: Jul. 28, 2003

(65) Prior Publication Data

US 2004/0077100 A1 Apr. 22, 2004

Related U.S. Application Data

(60) Provisional application No. 60/401,021, filed on Aug. 2, 2002.

(51) Int. Cl.
*C12Q 1/68* (2006.01)

(52) U.S. Cl. .............................. 435/6; 435/4; 436/523; 436/164

(58) Field of Classification Search ........... 435/6–7.23, 435/19, 91.1, 172, 196, 320.1; 514/44, 221; 534/727; 424/93.2, 94.6; 530/334
See application file for complete search history.

(56) References Cited

U.S. PATENT DOCUMENTS 5,037,207 A * 8/1991 Tomei et al. ............... 356/444
5,405,783 A 4/1995 Pirrung et al.
5,445,934 A 8/1995 Fodor et al.
5,445,935 A 8/1995 Royer
5,582,981 A 12/1996 Toole et al.
5,631,169 A * 5/1997 Lakowicz et al. .......... 436/537
5,641,629 A 6/1997 Pitner et al.
5,641,633 A 6/1997 Linn et al.
5,744,305 A 4/1998 Fodor et al.
5,756,292 A 5/1998 Royer
5,792,613 A 8/1998 Schmidt et al.
5,800,989 A 9/1998 Linn et al.
5,840,867 A 11/1998 Toole et al.
5,989,823 A 11/1999 Jayasena et al.
6,074,609 A 6/2000 Gavin et al.
6,166,804 A 12/2000 Potyrailo et al.
6,172,218 B1 1/2001 Brenner (Continued)

FOREIGN PATENT DOCUMENTS

WO WO 00/61803 10/2000

(Continued)

OTHER PUBLICATIONS

Spridonova et al, DNA aptamers as radically new recognition elements for biosensors, Jun. 2002, Biochem, 67, 706-709.*

(Continued)

*Primary Examiner*—Long V. Le
*Assistant Examiner*—N Yang
(74) *Attorney, Agent, or Firm*—Knobbe Martens Olson & Bear LLP

(57) ABSTRACT

The present invention relates to methods for detecting the presence of one or more analytes of interest in a sample by measuring changes in fluorescence anisotropy as a result of binding of the analytes to specific aptamers. The aptamers are immobilized on a solid support and may be in the form of an array.

20 Claims, 4 Drawing Sheets

U.S. PATENT DOCUMENTS

| | | | | |
|---|---|---|---|---|
| 6,242,246 | B1 | 6/2001 | Gold et al. | |
| 6,261,783 | B1 | 7/2001 | Jayasena et al. | |
| 6,297,018 | B1 * | 10/2001 | French et al. | 435/6 |
| 6,309,701 | B1 | 10/2001 | Barbera-Guillem | |
| 6,327,410 | B1 | 12/2001 | Walt et al. | |
| 6,365,418 | B1 | 4/2002 | Wagner et al. | |
| 6,399,302 | B1 | 6/2002 | Lannigan et al. | |
| 6,423,493 | B1 | 7/2002 | Gorenstein et al. | |
| 6,544,776 | B1 * | 4/2003 | Gold et al. | 435/287.2 |
| 6,573,045 | B1 | 6/2003 | Karn et al. | |
| 6,576,419 | B1 * | 6/2003 | Wei et al. | 435/6 |
| 6,610,504 | B1 | 8/2003 | Yuan | |
| 6,680,377 | B1 * | 1/2004 | Stanton et al. | 536/22.1 |
| 2001/0033374 | A1 | 10/2001 | Hoyt | |
| 2002/0037506 | A1 | 3/2002 | Lin et al. | |
| 2002/0061531 | A1 | 5/2002 | Xiao-Chun | |

FOREIGN PATENT DOCUMENTS

| | | |
|---|---|---|
| WO | WO 00/70329 | 11/2000 |
| WO | WO 01/57259 | 8/2001 |
| WO | WO 02/010750 | 2/2002 |
| WO | WO 02/24959 | 3/2002 |
| WO | WO 02/030561 | 4/2002 |

OTHER PUBLICATIONS

Fang et al, Molecular aptamer for real-time oncoprotein platelet derived growth factor monitoring by fluorescence anisotropy, 2001, 73, 5752-5757.*

Hesselberth et al, In vivo selection of nucleic acids for diagnostic applications, 2000, Rev Mol Biotech, 74, 15-25.*

Lee et al, A fiber-optic microarray biosensor using aptamers as receptors, 2000, Anal Biochem, 282:142-146.*

Lakowicz et al, Anisotropy-based sensing with reference fluorophores, 1998, Anal Biochem, 267, 397-405.*

Sevenich et al., "DNA binding and oligomerization of NtrC studied by fluorescence anisotropy and fluorescence correlation spectroscopy," Nucleic Acids Research, 1998, vol. 26, No. 6, pp. 1373-1381.

Hesselberth et al., "In vitro selection of nucleic acids for diagnostic applications," Reviews in Molecular Biotechnology 74 (2000) 15-25, Elsevier.

Potyrailo et al., "Adapting Selected Nucleic Acid Ligands (Aptamers) to Biosensors," Anal. Chem. 1998, 70, pp. 3419-3425.

Chinnapen et al, "Hemin-Stimulated Docking of Cytochrome c to a Hemin-DNA Aptamer Complex," Biochemistry 2002, 41, pp. 5202-5212.

Yeakley et al., "Profiling alternative splicing on fiber-optic arrays," Nature Biotechnology, Apr. 2002, vol. 20, pp. 353-358.

Zhou H, et al., "Solution and chip arrays in protein profiling." Trends in Biotechnology Oct. 19, 2001(10 Suppl):S34-9.

Jhaveri et al. "In Vitro Selection of Phosphorothiolated Aptamers" Nature Biotechnology, Dec. 2000, 18(12): 1293-1297.

Supplementary European Search Report, European Patent No. 03766936.3, European Patent Office. Jan. 22, 2007, 4 pages.

* cited by examiner 0.5% SDS
250 nM Lysozyme
Anisotropy
0.16
0.14
0.12
0.1
0.08
Time (sec)
0
500
1000
1500
2000
2500

FLUORESCENCE POLARIZATION ASSAY

REFERENCE TO RELATED APPLICATIONS

The present application claims priority under 35 U.S.C. §119(e) to U.S. Provisional Application No. 60/401,021, filed Aug. 2, 2002.

FIELD OF THE INVENTION

The present invention relates to methods for detecting the binding of analytes of interest to aptamers by measuring changes in fluorescence anisotropy.

DESCRIPTION OF THE RELATED ART

The introduction of immunoassays in 1959 and the enzyme-linked immunosorbent assay (ELISA) in 1971 revolutionized clinical diagnostic medicine. Until recently, molecules capable of molecular recognition, and therefore useful in diagnostic assays, have been limited to antibodies. The recent development of in vitro methods to select high affinity ligands by combinatorial chemistry methodologies promises unique novel therapeutics and diagnostic reagents. These methods allow for the identification of a large number of different oligonucleotide sequences with high affinity and specificity. For example, oligonucleotide sequences can be identified by the systematic evolution of ligands by exponential enrichment (SELEX™), a general method for identification of oligonucleotide ligands, also known as aptamers, as potential drugs. In this method, a pool of RNAs, completely randomized at particular positions, is subjected to selection for binding to a particular nucleic-acid binding protein which has been immobilized onto a nitrocellulose filter. The bound RNAs or DNAs are then recovered and further amplified as DNA. The DNA may be subjected to further characterization. These oligonucleotides can be used as probes for the identification of a variety of analytes, particularly proteins including various enzymes of HIV, growth factors and inflammation-inducing enzymes (Sun, S., *Curr. Opin. Mol. Ther*., 2(1):100–5 (2000)).

The platforms that have typically been used to identify and quantify aptamers bound to analytes are very limited in that they require a method for separating the bound product from one or both unbound reactants. Examples for separating the bound product from unbound reactants include binding to a solid phase, liquid chromatography and electrophoresis.

SUMMARY OF THE INVENTION

In one aspect, the present invention provides a method for detecting an analyte in a sample. A fluorophore-labeled aptamer bound to a solid support is contacted with the sample and illuminated with polarized light. The fluorescence anisotropy of the fluorophore is measured. and the presence of the analyte is identified when the fluorescence anisotropy value is greater than an anisotropy value obtained in the absence of the sample.

In one embodiment the solid support to which the fluorophore-labeled aptamer is bound is a bead, such as a silica bead. The bead may have a diameter between about 1 μm and about 10 μm. In a particular embodiment the bead has a diameter of about 5 μm. The bead may be suspended in solution or arranged in a two-dimensional array.

In another embodiment the aptamer is labeled with a fluorophore selected from the group consisting of fluorescein derivatives, eosin derivatives, coumarin derivatives and rhodamine derivatives. In a particular embodiment the fluorophore is carboxyfluorescein.

The aptamer may be part of an array of aptamers. In one embodiment the array of aptamers comprises two or more addressable locations. Each addressable location may comprise a single type of aptamer. In another embodiment each addressable location comprises multiple types of aptamers.

In one embodiment the polarized light used to illuminate the aptamer is laser light.

In another embodiment the analyte of interest is associated with a disease or disorder. The sample may be obtained from a patient suspected of suffering from a disease or disorder.

In one embodiment the analyte is a protein. In another embodiment the analyte is a metabolite.

In another aspect, a sample is obtained from a patient suspected of suffering from a disease or disorder. An analyte is identified that is associated with the disease or disorder and the presence or absence of the analyte is determined in the sample. The patient is diagnosed as suffering from the disease or disorder if the analyte is determined to be present in the sample taken from the patient.

DETAILED DESCRIPTION OF THE PREFERRED EMBODIMENT

Figure 1:
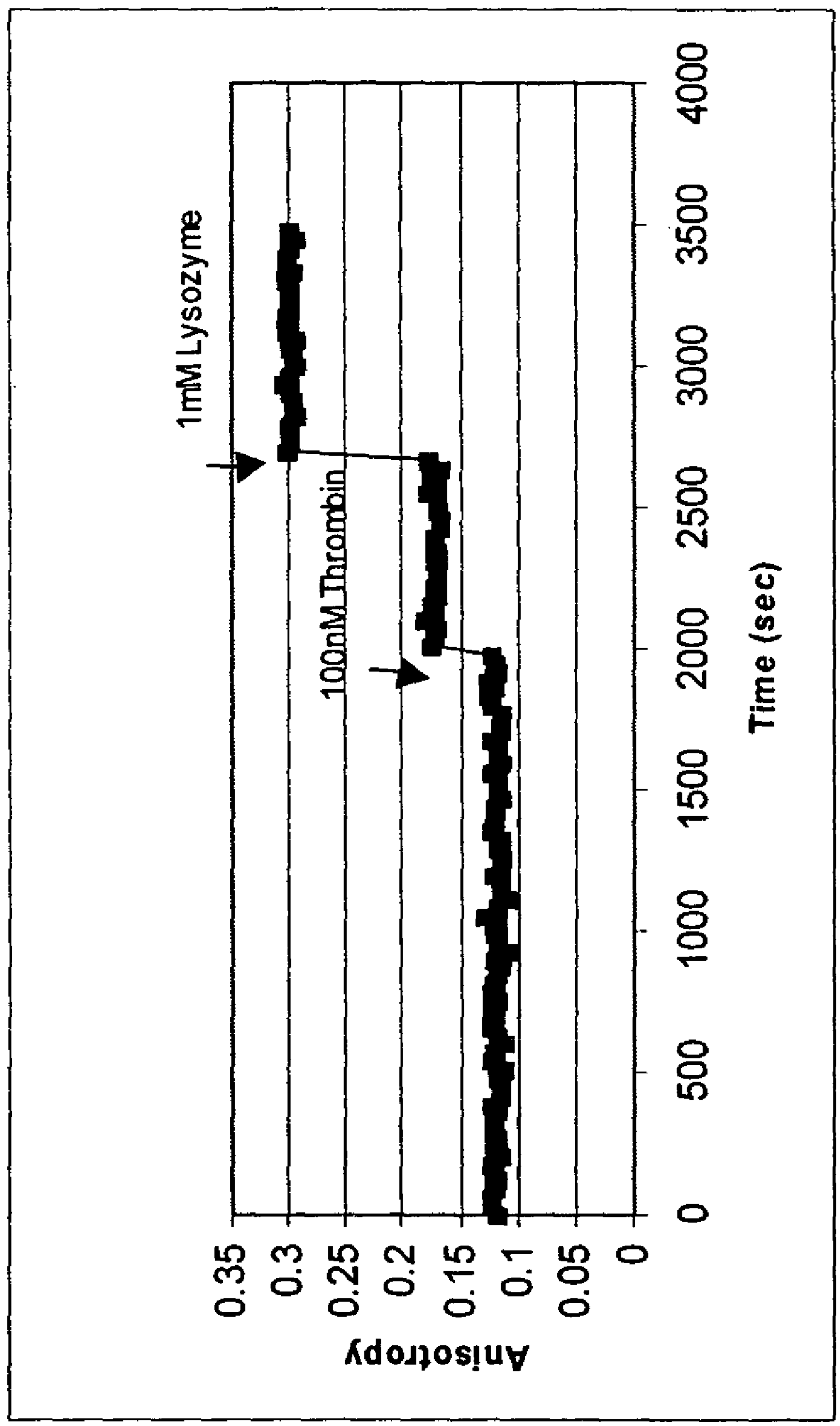
FIG. 1 shows kinetic data of binding of thrombin and lysozyme to FAM-labeled anti-thrombin aptamer coupled beads.

In one aspect, the present invention provides methods of identifying one or more analytes in a sample by measuring changes in fluorescence anisotropy resulting from the binding of the analytes to a labeled aptamer.

Definitions

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or a by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

A large number of aptamers are known in the art, and may be selected for use in particular applications based on their known properties. Alternatively, new aptamers may be prepared and identified by selection from random pools of oligonucleotides based on their ability to bind the specific molecule of interest. For example, new aptamers may be prepared and identified by the Systematic Evolution of Ligands by Exponential Enrichment (SELEX™) process, described, for example, in U.S. Pat. Nos. 5,475,096 and 5,270,613.

The aptamers are labeled with one or more fluorophores. A fluorophore may also be referred to as a fluorescent probe or dye. A "fluorophore" is any molecule that when excited with light of a particular wavelength, emits light of a different wavelength. Fluorophores include, but are not limited to, fluorescein (U.S. Pat. Nos. 5,188,934; 6,008,379; 6,020,481), eosin, coumarin, rhodamines (U.S. Pat. Nos. 5,366,860; 5,847,162; 5,936,087; 6,051,719; 6,191,278), such as tetramethylrhodamine, benzophenoxazines (U.S. Pat. No. 6,140,500), Texas Red and dansyl derivatives. Fluorescent reporter dyes useful for labeling biomolecules include energy-transfer dye pairs of donors and acceptors (U.S. Pat. Nos. 5,863,727; 5,800,996; 5,945,526), and cyanines (Kubista, WO 97/45539), as well as any other fluorescent label capable of generating a detectable signal. Examples of fluorescein dyes include 5-carboxyfluorescein ("FAM"), 6-carboxyfluorescein ("6-FAM"); 2',4',4,7,-tetrachlorofluorescein; and 2',4',5',7',4,7-hexachlorofluorescein. See U.S. Pat. No. 5,118,934.

The fluorophore may be incorporated into the aptamer at any position. For example, the aptamer may be labeled along its backbone, at a position in the bases, or at either end. The aptamer may be labeled by any method known in the art, such as by using standard DNA synthesis techniques using fluorescently labeled linker compounds. Alternatively, unlabeled linker compounds can be used during synthesis and subsequently labeled with a fluorophore. (See, for example, Ruth, J. (1991) Oligo and Analogues, pp. 255–282, Eckstein, F, Ed., IRL Press, Oxford, UK; Vinayak R. (1999) Tetrahedron Lett. 40:7611–7813.) When aptamers are prepared by the SELEX™ process, the fluorophore may be incorporated into the selection process to insure that the fluorophore does not perturb binding of the analyte to the aptamer. In addition, identification of fluorophore positions that are part of the aptamer binding domain may insure that binding of the analyte results in a significant change in fluorescence anisotropy.

A "label" is any moiety which can be attached to a polynucleotide and provide a detectable signal, such as a fluorophore.

"Fluorescence" is the emission of light from a sample or dye, which is longer in wavelength than light which falls on the sample or dye. The light falling on the sample or dye, usually referred to as the "excitation" light, is absorbed by the sample or dye and then emitted as "emission" light.

"Anisotropy" is the difference in the property of a system with changes in direction. In the context of "fluorescence anisotropy," this means a difference in the polarization of the emission light, as hereinabove defined.

As used herein, the terms "polynucleotide" and "oligonucleotide" are used interchangeably and mean single-stranded, double-stranded and triple-stranded polymers of nucleotide monomers, including 2'-deoxyribonucleotides (DNA) and ribonucleotides (RNA). A polynucleotide may be composed entirely of deoxyribonucleotides, entirely of ribonucleotides, or chimeric mixtures thereof. Polynucleotides may be comprised of internucleotide, nucleobase and sugar analogs, including unnatural bases, sugars, L-DNA and modified internucleotide linkages.

"Linker" refers to a chemical moiety in a molecule comprising a covalent bond or a chain of atoms that covalently attaches one moiety or molecule to another, e.g. a fluorophore to an aptamer or an aptamer to a solid support.

A linker may comprise a removable protective group. A "protective group" is a material which is bound to a molecule and may be removed upon selective exposure to an activator, such as light.

The term "solid support" refers to any solid phase material upon which an aptamer may be attached or immobilized. For example, a solid support may comprise glass, metal, silicon, germanium, GaAs, or plastic. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, a fiber or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array.

"Array" or "microarray" means a predetermined spatial arrangement of aptamers present on a substrate. The aptamers may be directly attached to the substrate, or may be attached to a solid support that is associated with the substrate. The aptamers may all be identical, as in the case of an array that is designed to detect a single analyte, or the aptamers may be different, such as in an array that is designed to detect and/or identify a variety of different molecules in a sample. The array may comprise one or more "addressable locations," that is, physical locations that comprise a known type of aptamer. In one embodiment an addressable location comprises more than one type of aptamer. However, the types of aptamers present at each location are known or may be determined.

An array can comprise any number of addressable locations, e.g. 1 to about 100 (low number), 100 to about 1000 (medium number) or a thousand or more (high number). In addition, the density of the addressable locations on the array may be varied. For example, the density of the addressable locations on a substrate may be increased to reduce the necessary substrate size. Typically, the array format is a geometrically regular shape, which may facilitate, for example, fabrication, handling, stacking, reagent and sample introduction, detection, and storage. The array may be configured in a row and column format, with regular spacing between each location. Alternatively, the locations may be arranged in groups, randomly, or in any other pattern. In one embodiment an array comprises a plurality of addressable locations configured so that each location is spatially addressable for high-throughput handling.

In a two-dimensional array the addressable location is determined by location on the surface. However, in one embodiment the array comprises a number of particles, such as beads, in solution. Each particle comprises a specific type or types of aptamer. In this case the identity of the aptamer may be determined by the characteristics of the particle. For example, the particle may have an identifying characteristic, such as shape, pattern, chromophore, or fluorophore.

"Target" and "analyte" both refer to a specific molecule or compound, the presence, absence or amount of which is to be detected, and that is capable of interacting with an aptamer. The analyte may be any molecule, including, without limitation, a polypeptide, protein, protein complex, oligonucleotide, DNA, RNA, carbohydrate, polysaccharide, metabolite, nutrient, drug or small molecule. The analyte may be naturally occurring or synthetic. In one embodiment an analyte is a polypeptide derived from a living, or once living, organism, including but not limited to prokaryote, eukaryote, plant, animal, and virus.

"Substrate" when used herein refers to the underlying core material of the arrays of the invention. Typically the substrate is a solid support and has a rigid or semi-rigid surface. In one embodiment the surface of the substrate is flat. In other embodiments the surface of the substrate may comprise physical features, such as wells, trenches and raised or sunken regions. The aptamers that form the array may be attached directly to the substrate, or may be attached to a solid support that is itself associated with, such as attached to or contained by, the substrate.

Exemplary Modes for Carrying Out the Invention

The present invention provides methods for determining the presence, absence or quantity of one or more analytes in a sample based on changes in fluorescence anisotropy upon binding of an analyte to a fluorescently labeled aptamer. Fluorescence anisotropy arises from fluorescence polarization, which reveals the average angular displacement of the fluorophore, which occurs between absorption and subsequent emission of a photon.

As discussed above, the analytes are not limited in any way, and thus the methods disclosed herein are broadly applicable to many different fields. The identity of the analytes will vary depending on the nature of the analysis and one of skill in the art in a particular field will be able to adapt the methods to their specific circumstances.

The presence or absence of one or more analytes is determined in a sample. The sample may be any composition that is desired to be analyzed for the presence of an analyte and is not limited in any way. For example, without limitation, in a medical setting it may be desirable to analyze a sample of bodily fluid, such as blood, from a patient for the presence of a polypeptide associated with a disease or disorder, such as an infectious agent, while in an industrial setting it may be desirable to analyze a waste stream for the presence of a particular organic compound.

Aptamers that are specific for the analytes of interest are identified. The aptamer may be one that has been previously identified as capable of binding the analyte of interest. Many such aptamers are known in the art. For example, a database of aptamers with known selectivity is maintained at the University of Texas at Austin (http://aptamer.icmp.utexas.edu). A number of different aptamers can also be obtained commercially, such as from Somologic (Colorado, USA) or Gilead Sciences, Inc. (California, USA). If an aptamer that is specific for the analyte of interest has not been described previously, it can be identified by any method known in the art. Methods for identifying aptamers that interact with specific compounds are well known. For example, an aptamer that is specific for a particular ligand can be identified by the Systematic Evolution of Ligands by Exponential Enrichment (SELEX™) process, described, for example, in U.S. Pat. Nos. 5,475,096 and 5,270,613. In the SELEX™ process a pool of randomized RNA or single stranded DNA sequences are selected against a desired target. The sequences that show tighter binding with the target are isolated and amplified. The selection is repeated several times using the enriched pool derived from the previous round of selection to identify useful aptamers.

Once an aptamer has been identified, one or more copies of the aptamer are produced for use in the assay to detect the presence of the analyte. The aptamers may be produced by any method known in the art. Thus, they may be chemically synthesized by standard procedures. The aptamers may be labeled with a fluorophore, either during or after synthesis. They may be labeled by any method known in the art. For example, the aptamer may be labeled by incorporation of a modified nucleotide during synthesis. Alternatively, the aptamer may be chemically modified after synthesis. Following labeling, the aptamers are contacted with the sample to be analyzed. In another embodiment, the label can be incorporated during the SELEX™ process. This may help to place the label within the binding site for the analyte, which in turn will ensure the greatest change in fluorescence anisotropy upon analyte binding.

The aptamers are typically present on a solid support when they are contacted with the sample to be analyzed. The aptamers can be synthesized directly on the solid support, or, alternatively, the aptamers may be bound to the solid support following synthesis. See, for example, Southern et al., Nuc. Acids Res., 20(7):1679–1684 (1992); Southern et al., Genomics, 13:1008–10017 (1992); WO02/30561; WO02/0750; WO96/40790; Maclean et al. Proc. Natl. Acad. Sci. USA 94:2805–2810 (1997); and U.S. Pat. Nos. 5,744,305, 5,405,783, 5,445,934 and 6,261,776. The aptamers may be bound to the solid support by any method known in the art. For example, 3'-amine-modified aptamers may be applied to activated surfaces of the solid support (Potyrailo et al., *Analytical Chemistry*, 70(16):3419–3425 (1998)). In one embodiment a glass substrate is activated with (glycidoxypropyl) trimethoxy silane (GOPS). Fluorescently labeled aptamers, modified by attachment of an alkylamino group to the 3' end, are subsequently covalently bound to the glass substrate. Unreacted aptamers may be removed by washing, and unreacted surface groups may be blocked. In one embodiment unreacted surface groups are blocked by an incubation with 0.1 M ethanolamine solution. In another particular embodiment, aptamers with C6-aminolinker at the 5' end are bound to treated silica particles.

In another embodiment the aptamers are attached to a solid support via linker molecules. Linker molecules are provided on the surface of the substrate. The linker molecules are then contacted with the aptamers under conditions such that the aptamers are bound to the substrate via the linker molecules.

In a particular embodiment, arrays of aptamers are formed on a substrate comprising linker molecules wherein the distal ends of the linker molecules comprise a functional group with a protective group. The formation of such arrays is described, for example, in U.S. Pat. Nos. 5,445,934, 5,744,305 and 5,405,783, the disclosures of which are incorporated herein by reference. The protective group may be removed to expose the functional group by exposing the linker molecule to the proper conditions, such as light, radiation, electric fields, electric currents or other activators. By directing the activator to particular linker molecules, a defined portion of the substrate can be activated. For example, if the protective group is removable by light, a defined region of the substrate may be illuminated, thus activating the linker molecules in that area. A particular type of aptamer may then be contacted with the activated linker molecules. Excess aptamer is then removed and any unreacted linker molecules are blocked. In this way, an addressable location comprising a particular type of aptamer is produced. A different discrete area of linker molecules on the substrate may then be activated. A second type of aptamer may then be bound to the second discrete area. By repeating this process an array comprising a number of addressable locations comprising known aptamer types may be formed on the substrate. In an alternative embodiment, rather than attaching aptamers that have been previously synthesized, aptamers can be synthesized directly on the activated areas of the substrate.

The aptamers may be bound to a solid support that is suspended in solution. For example, the aptamers may be bound to beads that are subsequently suspended in buffer. In one embodiment the beads are suspended in wells, such as in the wells of a microtiter plate. Each well may contain beads that each comprise the same type of aptamer. In this way, multiple samples may be analyzed simultaneously for the presence of a single analyte. In another embodiment each well contains beads that comprise a different type of aptamer, to allow for detection of a variety of different analytes. In yet another embodiment, each well contains beads comprising a variety of different aptamers, allowing for the determination of the presence of one or more of a variety of analytes.

The presence of an analyte of interest in a sample is determined by identifying a change in the fluorescence anisotropy of the fluorophore attached to the aptamer upon binding of the analyte to the aptamer. Baseline fluorescence anisotropy in the absence of the analyte is measured, as described below. Subsequently, the aptamer is contacted with the sample to be analyzed for the presence of the analyte and fluorescence anisotropy is again measured. The presence of the analyte is indicated by observation of a change in fluorescence anisotropy. Alternatively, the baseline fluorescence anisotropy can be determined from an aptamer-coated solid-phase that is run in parallel and is not subsequently contacted with sample.

Fluorescent intensities are determined for selected positions of the excitation and emission polarizers. The fluorophore bound to the aptamer is excited by illumination with polarized light. Any excitation source known in the art may be used. For example, light from a xenon arc lamp may be polarized and focused on the desired area. In another embodiment, a laser excitation source is used, thus eliminating the need for an excitation polarizer.

Fluorescent measurements may be made by any method known in the art, such as with single channel detection and in either right angle (90°), in T or L format, or front face emission collection geometry using a fluorescence spectrometer, for example, a Flurolog-3™ instrument, which is commercially available from SPEX (NJ, USA). See, for example, Lakowicz, "Principles of Fluorescence Spectroscopy," p. 111–153, Plenum Press, New York, N.Y. (1986) and Potyrailo et al. Anal. Chem. 70:3419–3425 (1998).

A typical apparatus for measuring the change in fluorescence anisotropy will thus comprise an excitation source, an excitation filter that passes the desired wavelength of light, a polarizing filter that polarizes the light from the excitation source prior to the excitation light contacting the aptamer(s), and a lens for focusing the excitation light on the aptamer(s) of interest, such as at an addressable location on a substrate.

In one embodiment, a laser is used. In this embodiment the polarizer and lens may not be required due to the nature of laser light.

The apparatus will also typically comprise a sample chamber, one or more emission polarizers to polarize the emitted light, an emission filter to pass the desired wavelength of emitted light and a detector for collecting and quantitating the amount of emitted light.

Fluorescence anisotropy arises from fluorescence polarization, which reveals the average angular displacement of the fluorophore, which occurs between absorption and subsequent emission of photon.

Fluorescence anisotropy (FA) is calculated from measurements of emission intensity, I, as $$FA=(I_{vv}-GI_{vh})/(I_{vv}+2GI_{vh}) \quad \text{(I)}$$

Where G is the instrumental correction factor, $G=I_{hv}/I_{hh}$ and the subscripts v and h refer to the vertical and horizontal orientation of the polarizer, respectively.

In one embodiment, measurements are taken with a detection time constant of about 1 s at a temperature of about 25° C.

The change in polarization anisotropy of the fluorophore labeled aptamer with time on binding to the analyte of interest may be determined in order to determine the kinetics of analyte binding to the aptamer.

The sensitivity of this method allows for the identification of small amounts of an analyte of interest in a sample. For example, for aptamers that bind to an analyte with high affinity, detection down to 1 to 10 pM of analyte is achievable.

Bead Arrays

Arrays of aptamers may be used to identify the presence of one or more analytes in a sample. In one aspect of the invention, the arrays comprise aptamers that are immobilized onto the surface of a substrate. In one embodiment, labeled aptamers that are specific for the analytes of interest are bound to microspheres or beads. The beads may then be used to form an array useful for the detection of one or more analytes. See Walton et al. Analytic. Chem. 74:2240–2247 (2002); Zhou et al. Trends in Biotech. 19:S34–S39 (2001); WO02/24959; WO00/50903; WO00/61803 and U.S. Pat. Nos. 5,340,422 and 6,074,609.

The aptamer-attached beads may be free in solution or physically attached to or associated with a substrate. When free in solution, the fluorescence anisotropy may be measured in a flow cytometer. If the beads are attached to the surface of a solid support or substrate, they may be attached at particular sites to form an array with one or more addressable locations.

"Microspheres" or "beads" are small discrete particles. While the beads generally have a spherical geometry, their shape may be irregular. In one embodiment the irregular size or shape identifies a bead as comprising a particular type of aptamer. Typically beads have a diameter from about 1 μm to about 10 μm. Alternatively they may have a diameter from about 10 nm to about 1 mm, or even from about 10 nm to about 100 μm. The beads may be comprised of any material to which an aptamer may be bound, including, without limitation, plastic, glass, ceramic, metal, cellulose, nylon or latex.

The number of aptamers on a single bead is not limited in any way. Typically, however, each bead will comprise at least about $10^5$ aptamers. Each bead may comprise a single type of aptamer. Alternatively, however, each bead may comprise more than one type of aptamer. This may be useful, for example, if the presence of at least one of a number of compounds is to be determined in a sample, and it is not necessary to know which particular compound is present. In another embodiment, each bead may contain several different types of aptamers, each comprising a different fluorophore. In such a manner, each bead may be capable of detecting multiple analytes.

The aptamers may be synthesized directly on the beads, or may be made and subsequently attached to the beads using linker molecules. For example, the surface of the bead may be modified to allow the attachment of the aptamer, such as with a chemically reactive group like a thiol or an amine. Such modifications are well known in the art. The aptamers bound to the beads may be fluorescently labeled before or after attachment to the beads.

The aptamer-coupled beads may be used to detect the presence of one or more analytes in a sample. Aptamer-coupled beads may themselves be attached to a solid support. Typically however, the beads are placed in solution in a vessel, for example, a cuvette or a well of a microtiter plate.

An array of beads may be used to detect a single analyte in a sample. In this case, all of the beads in the array will be of the same type and thus will typically be derivatized with the same type of aptamer.

In one embodiment, beads labeled with fluorescently labeled aptamers that are specific for the analyte of interest are placed in solution in a vessel, for example a cuvette or a well of a microtiter plate. A sufficient number of aptamer-coupled beads must be present to generate a detectable signal. At least about $10^6$ beads are generally present in solution in the vessel. The sample to be analyzed is added to the vessel. Fluorescence anisotropy is measured as described above, both before and after addition of the sample. A change in fluorescence anisotropy following addition of the sample is indicative of the presence of the analyte in the sample.

For the simultaneous analysis of multiple samples for the presence of a single analyte, a number of vessels may be used. A number of individual vessels, such as a number of cuvettes, can be used. Alternatively, the vessels can be associated with each other to facilitate rapid handling, such as in a multi-well microtiter plate. In one embodiment, each well of a multi-well microtiter plate comprises the same type of aptamer-coupled beads in solution. The samples are then added to the wells, one sample per well. Fluorescence anisotropy is measured in each well before and after addition of the sample, A change in fluorescence anisotropy upon addition of the sample is indicative of the presence of the analyte in the sample. Samples that were added to wells in which a change in fluorescence anisotropy was measured are identified as comprising the analyte of interest.

An array comprising aptamer-coupled beads may also be used to determine if one or more of a variety of different analytes are present in a sample. In this embodiment a number of different types of aptamers, equal to or greater than the number of analytes to be identified, will be represented in the population of beads.

Typically, the identity of any analytes present is of interest. Thus, it is necessary to identify the type of aptamer on each bead at each location in the array so that the binding of different analytes can be distinguished. This may be achieved by individually placing beads with known aptamers in the array. Alternatively, the beads may be randomly distributed in the array and the specific location of individual beads in the array determined after the array is formed. This may be accomplished by any method known in the art. For example, the beads may be coded such as with a fluorophore, bar-code, IR tag. In one embodiment a fluorescently labeled oligonucleotide that is complementary to a particular aptamer sequence may be used to determine the exact location of beads that comprise that aptamer.

In one embodiment, an array is used to detect the presence of two or more analytes in a sample. Aptamer-coupled beads are prepared that are specific for each analyte to be detected. The different types of aptamer-coupled beads are then placed into solution in separate vessels, so that each vessel contains only beads comprising aptamers that are specific for a particular analyte. In one embodiment, the aptamer coupled beads are placed in solution in the wells of a microtiter plate. The location of the wells comprising specific types of aptamer-coupled beads is noted. A particular sample of interest is then divided between each of the wells comprising a specific type of aptamer coupled beads. The fluorescence anisotropy is measured in each well before and after addition of the sample. The identity of analytes that are present in the sample can then be determined by comparing positive results, i.e. a change in fluorescence anisotropy, to the noted location of the particular types of aptamer coupled beads.

In another embodiment, aptamer coupled beads are physically attached to a substrate to form a two-dimensional array. The beads may be attached in such a way that beads comprising the same type of aptamer are localized together in addressable locations. The different types of beads may be separated by a physical barrier, such as by localization in different wells of a microtiter plate. Alternatively, the different types of beads may be spatially separated. The analyte specificity of the beads in each location is noted or determined. The sample is contacted with the beads and any change in fluorescence anisotropy is determined for each addressable location in the array. The addressable locations that are associated with a change fluorescent anisotropy are identified, and the presence of a particular analyte in the sample is determined based on the analyte specificity of the aptamers at those location in the array.

In an alternative embodiment the presence of one or more analytes from a group of analytes is to be determined in a sample without determining the specific identity of the analytes that are present. In this case, it is not necessary to separate the types of beads in the array. However, localization of the same types of beads together in the array may produce an increased signal and thus facilitate detection of smaller quantities of the analytes of interest.

Non-Bead Arrays

In non-bead arrays, aptamers are arranged directly on a substrate for use in the detection of one or more analytes. Non-bead arrays are described, for example, in U.S. Pat. Nos. 5,445,934, 5,405,783, 5,744,305, 6,365,418, The aptamers may be attached to the substrate via linkers, using methods well known in the art. Alternatively, the aptamers may be synthesized directly on the substrate.

In a typical array a substrate comprises one or more addressable locations of aptamers. The addressable locations may be directly adjacent to each other or may be physically separated by a gap or a barrier. In one embodiment, the addressable locations are sufficiently separated that illumination of one addressable location for the determination of fluorescence anisotropy will not illuminate any part of an adjacent location. Thus, if the area of illumination is smaller than the addressable location of aptamers, the addressable locations may be directly adjacent, without any space in between. On the other hand, if the size of the addressable locations is smaller than the minimum area of illumination, the distance between the locations will be large enough to prevent overlapping illumination.

Typically, each addressable location comprises one type of aptamer. However, in one embodiment, at least one addressable location comprises more than one type of aptamer. This arrangement is useful, for example, if the presence of one of a number of analytes is to be determined, and the identity of the particular analyte is not of concern. Alternatively, multi-plex analyte detection can be accomplished using a set of aptamers, each with a different fluorophore, attached at the same location. Each of the fluorophores has different spectral characteristics, allowing the binding of multiple analytes to be distinguished.

In other embodiments, each addressable location comprises a single type of aptamer. In this case, the number of locations on the array of aptamers is at least as great as the number of different types of aptamers to be used, and thus at least as great as the number of analytes to be detected. For example, if the presence of ten analytes is to be detected in a sample, at least ten addressable locations of aptamers will be present on the substrate. The number of addressable locations is not limited in any way and will be determined, for example, by the number of analytes to be detected and the physical size of the substrate on which the array is formed. In one embodiment, each addressable location comprises at least about $10^5$ aptamers.

Typically, the aptamer composition and physical location of each addressable location is known. In one embodiment, each of the addressable locations in the array comprises a different type of aptamer. For example, if ten analytes are to be assayed for, the array will comprise ten addressable locations, each comprising a different type of aptamer. In an alternative embodiment, more than one addressable location comprising a particular type of aptamer is present.

The addressable locations of aptamers in the array may be any geometric shape. For example, the addressable locations may be circular, rectangular, square or irregularly shaped. Typically the shape of the addressable locations will be chosen to facilitate attachment of the aptamers to the substrate and determinations of fluorescence anisotropy.

The overall size of the array is not limited and will be determined based on a variety of factors, including the number of aptamers in each addressable locations, the number of addressable locations, and physical constraints on the size of the substrate arising from the system used to detect changes in fluorescence anisotropy. In one embodiment, the addressable locations of the array are all present on a substrate with an area of about 100 $cm^2$ or less. In another embodiment the discrete areas of the array are all present on a substrate with an area of about 10 $cm^2$ or less.

For detecting the presence of one or more analytes in a sample, the sample is contacted with the array of aptamers. Each of the addressable locations of aptamers is individually illuminated with polarized light before and after contacting the sample and any change in fluorescence anisotropy is determined. If a change in fluorescence anisotropy is measured for any particular addressable location of aptamers, the compound with which that particular type of aptamer interacts is identified as being present in the sample.

Exemplary Applications

The analysis of samples for the presence of one or more particular analytes finds uses in a wide range of fields, from medical, basic biological research, pharmaceutical, agricultural, environmental and industrial diagnostics to proteomics.

In another embodiment, the arrays of the invention may be useful for diagnostic applications and for use in diagnostic devices. In one embodiment the arrays are used to establish a correlation between the expression level of a particular protein and a disease or a particular stage of a disease. In a further embodiment, once such a correlation between the expression level of a protein and a particular disease or a particular stage of a disease has been made, or is known, the arrays of the invention may be used to diagnose a particular disease or a stage of a disease in a tissue of an organism. Accordingly, in one embodiment, the invention provides a method of diagnosing a disease or disorder in a patient. One or more analytes that are known to be associated with the disease or disorder from which a patient is believed to be suffering are selected. For example, if a patient is suspected of suffering from a tumor, the methods of the present invention may be used to identify the presence of one or more proteins that are known to be expressed in tumor cells, but not in normal cells. Similarly, if a patient is suspected of having been exposed to an infectious agent, proteins known to be associated with the infectious agent are selected for identification. For example, a sample from a patient suspected of being infected with HIV may be analyzed for the presence of protein known to be associated with HIV, such as GP120MN.

Aptamers that specifically recognize the selected analytes are identified and synthesized. The aptamers are fluorescently labeled and attached to a solid support in an array format that allows for the identification of more than one analyte. Fluorescence anisotropy is measured as described above for each type of aptamer and the aptamers are then contacted with an appropriate sample from the patient. A change in the fluorescence anisotropy for a particular type of aptamer following contact with the sample is taken as indicative of the presence of the particular analyte for which that type of aptamer is specific.

Similarly, the assays of the invention may be used to evaluate the efficacy of a treatment regimen. For example, the presence of one or more analytes known to be associated with a disease or disorder may be assayed for in a biological sample from a patient prior to and after treatment. This may help determine the efficacy of particular treatment options.

In another embodiment, the invention provides a method of comparing the expression of particular proteins in two or more cells or populations of cells. Methods include assaying in parallel for a plurality of different proteins in a sample, such as expression products, or fragments thereof, of a cell or a population of cells from an organism. The methods involve incubating the sample to be analyzed for the presence of specific proteins to an aptamer array of the invention comprising aptamers that specifically bind the proteins of interest. The presence and/or amount of the proteins of interest in the sample is detected. Such methods optionally comprise the additional step of further characterizing the protein bound to at least one type of aptamer in the array. In addition, the presence of analytes other than proteins can be detected, for example metabolites.

The methods may involve the comparison of the protein expression pattern of a cell or population of cells, optionally subjected to different conditions, to the protein expression pattern of a control cell or population. For example, the protein expression pattern of a neoplastic cell may be compared to the protein expression pattern of a control cell or population. In a further example, the different conditions may include infecting one cell or population with a pathogen, exposing one cell or population to a stressor or exposing one cell or population to a drug, such as a potential therapeutic. For such comparison, a sample containing expression products, or fragments thereof, of the first cell or population of cells is incubated with an array of aptamers under conditions suitable for protein binding. In a similar manner, a sample containing expression products, or fragments thereof, of a second cell or population of cells is incubated with a second aptamer array that is identical to the first aptamer array. The types of proteins identified by changes in fluorescence anisotropy upon binding to the fluorescently labeled aptamers of the first aptamer array may be compared to the types of protein identified by the corresponding second aptamer array.

The methods of comparing the protein expression between two cells or two population of cells may be useful in the identification and validation of new potential drug targets, as well as for drug screening. In particular, the method may be used to identify a protein which is overexpressed in disease, such as tumor cells, but not in normal cells. Such a protein may be a target for drug intervention, such as with inhibitors targeted to such a differentially expressed protein.

The aptamer assays of the invention may further be used to evaluate the efficacy and specificity of a particular drug. For example, the expression pattern of particular proteins in a cell or population of cells that have been exposed to a particular drug may be compared to the expression pattern of a control cell or a population of cells that have not been exposed to the drug.

In another embodiment, the arrays may be used to establish a correlation between the expression of a particular protein and a disease or a particular stage of a disease.

One of skill in the art will be able to readily adapt the disclosed methods to particular uses.

EXAMPLES

The following examples are offered for illustrative purposes only, and are not intended to limit the scope of the present invention in any way.

All patent and literature references cited in the present specification are hereby incorporated by reference in their entirety.

Example 1

A. Methods for Assessing Binding of Proteins to Aptamer-Coupled Beads

The polarization anisotropy of dye-labeled aptamers changes with time upon binding to a specific protein. Changes in fluorescence anisotropy of 3 aptamers bound to a solid support upon binding of specific proteins was measured.

The three fluorophore labeled aptamers used in these experiments were anti-thrombin aptamer (FAM-labeled, a 15 mer), which is specific for thrombin from human plasma, 518-aptamer (FAM-labeled, a 60 mer), which is specific for GP120MN, an HIV-1 protein and 650-aptamer (FAM-labeled, a 60 mer), which is specific for recombinant human FGF basic protein.

1. Anti-Thrombin Aptamer for Thrombin

Binding of thrombin to FAM-labeled anti-thrombin aptamers was measured. 5 micron silica particles were purchased from Bangs Laboratories (OH, USA) and pretreated with 1N NaCl solution at 100° C. for 1 hour. The silica particles were then treated for 30 minutes with 3-aminopropyltriethoxysilane (APTES; Sigma, USA), diluted to 10 mM in 200 proof ethanol. After reaction, particles were washed with ethanol three times and dried at 60° C. in a Vacufuge (Eppendorf, Germany) overnight. Dried silanized particles were treated with 10 mM solution of Bis(thiopropyl N-hydroxy succinidimyl) (Sigma, USA) for 30 minutes in DMF at 40° C., followed by washing with DMF and ethanol quickly. A 15 mer anti-thrombin aptamer with C6-aminolinker at 5' and FAM at 3' was synthesized using an ABI304 synthesizer and subjected to HPLC purification. 10 mg of reactive silica beads with silane and NHS were incubated with 100 μm aptamer at 4° C. for 12 hours. Samples were washed and dried in a vacuum.

For polarization experiments, 100 mg/ml (about $1\times10^5$ particles) of FAM-labeled anti-thrombin aptamer coupled bead solution in phosphate buffered saline (PBS) was placed in a 160 μL quartz cuvette at ambient condition. The cuvette was placed in a SPEX Flurolog Fluorometer (NJ, USA) set to polarization mode. The samples were mixed well with a small magnetic stir bar during the experiment. Different concentrations of thrombin analyte were added to the aptamer-coupled bead solution The resultant polarization or anisotropy was plotted against time during the experiment.

2. 518-Aptamer for GP120MN Protein

Binding between GP120MN protein and 518 aptamer coupled to beads was examined. 518-aptamer with a C6-aminolinker at the 5' end and FAM at the 3' end was synthesized using an ABI394 synthesizer. Subsequently the labeled aptamer was HPLC purified. Reactive silica beads prepared as described above were treated with 100 μM labeled 518-aptamer at 40° C. for 12 hours. Samples were washed and dried in vacuum.

Polarization experiments using the FAM-labeled 518 aptamer coupled beads and GP120MN protein were performed as described above.

3. 650-Aptamer for Recombinant Human FGF Basic Protein

Binding between recombinant human FGF basic protein and 650 aptamer coupled to beads was examined. 650 aptamer with C6-aminolinker at 5' and FAM at 3' was synthesized using an ABI394 synthesizer and subsequently HPLC purified. Reactive silica beads prepared as described above were treated with 100 μM labeled 650-aptamer at 40° C. for 12 hours. Samples were washed and dried in vacuum.

Polarization experiments using the FAM-labeled 650 aptamer coupled beads and recombinant human FGF basic protein were performed as described above.

B. Results of Binding of Proteins to Aptamer-Coupled Beads

Binding of proteins to aptamers attached to 5 μm-sized particles as described above was assessed by fluorescence anisotropy. Fluorescence anisotropy was analyzed using 5'-aminated anti-thrombin aptamer that was 3'-FAM labeled and attached to silica beads. The thrombin aptamer-coupled particles were exposed to thrombin protein, and the change in fluorescence anisotropy was measured. An increase in anisotropy (FIG. 1) was observed upon addition of 100 nM thrombin. The change was similar to that observed upon binding of thrombin to thrombin aptamer in solution. Non-specific binding to lysozyme, a cationic protein that binds non-specifically to all aptamers, was also observed in the assay (FIG. 1).

Figure 2:
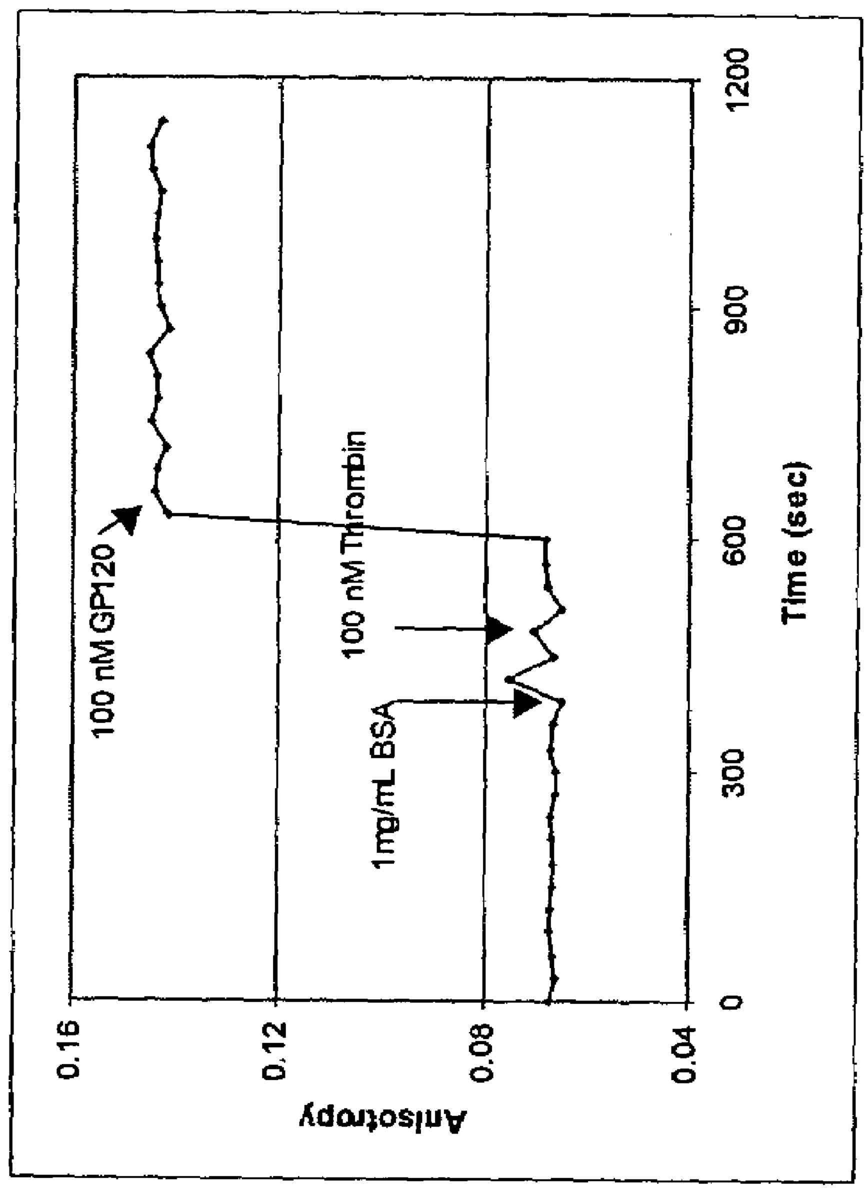
FIG. 2 shows kinetic data of binding of GP120 to FAM-518 aptamer coupled beads.
Figure 3:
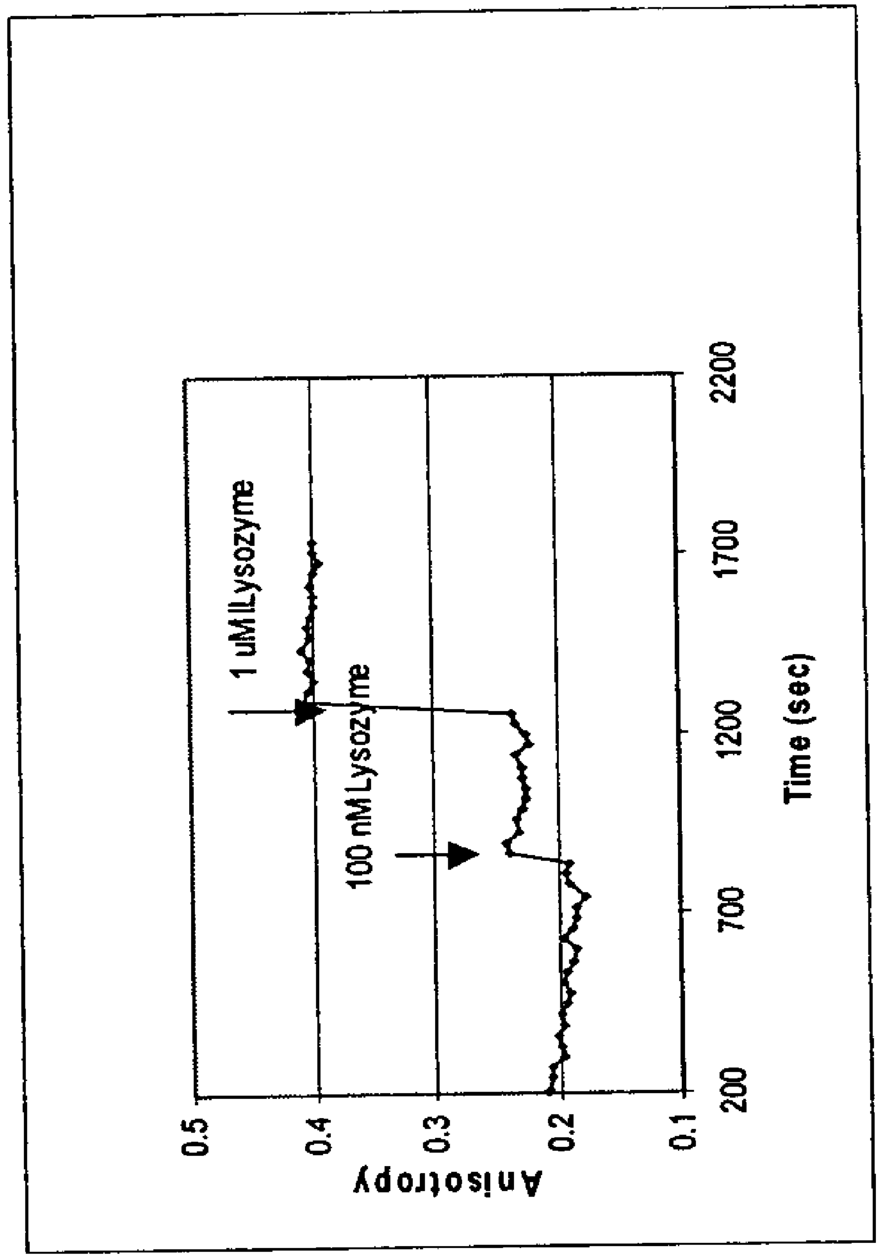
FIG. 3 shows kinetic data of binding of lysozyme to FAM-518 aptamer coupled beads.
Figure 4:
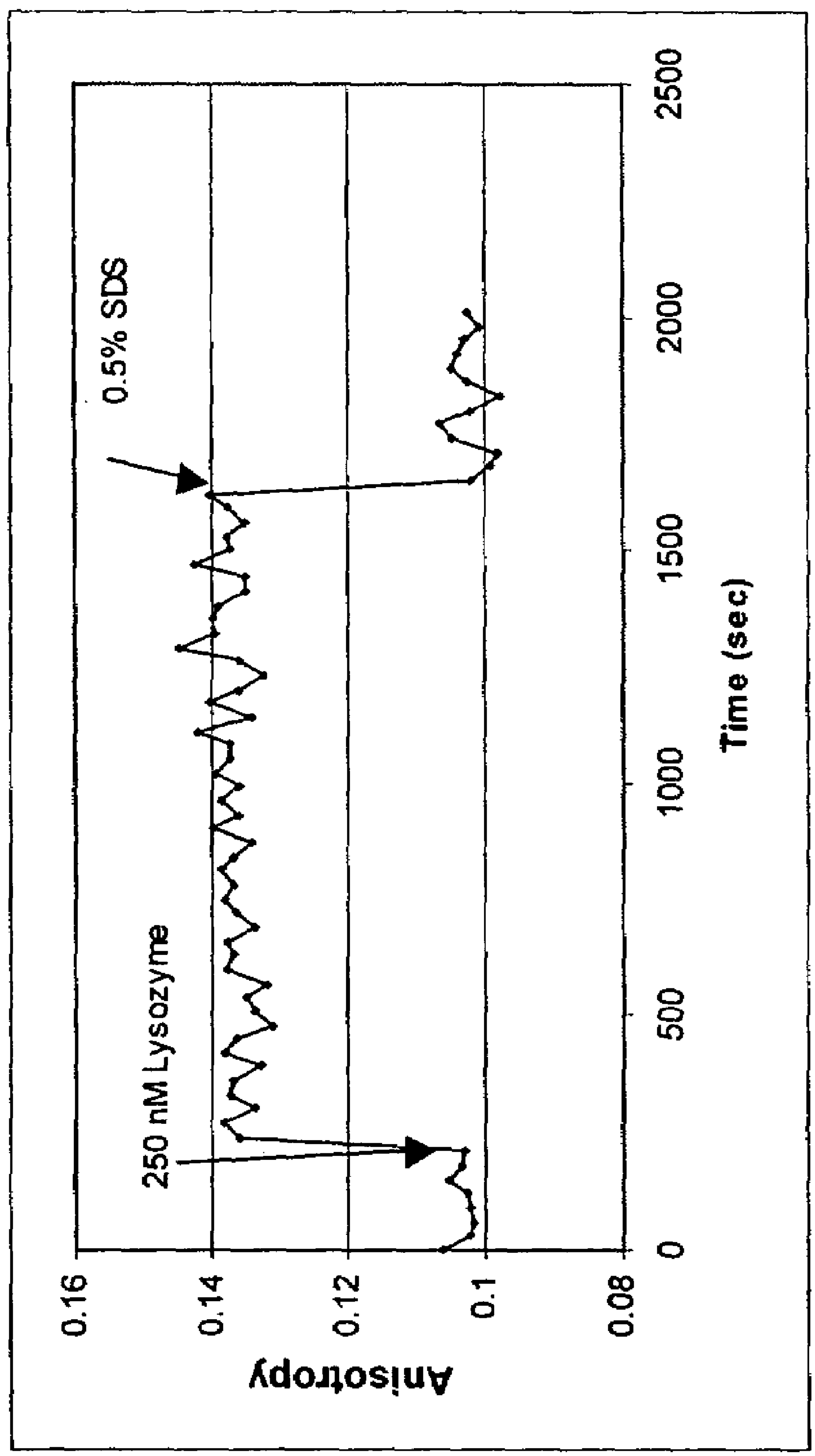
FIG. 4 shows kinetic data of reversible binding of lysozyme to FAM-518 aptamer coupled beads.

Aptamer 518 (60 mer) is specific for G120MN (HIV-1) protein. Upon addition of 100 nM GP120, a large increase in fluorescence anisotropy was observed (FIG. 2). the increase was significantly greater than, and easily distinguished from the small increase in fluorescence anisotropy that resulted from non-specific binding upon addition of 1 mg/ml BSA or 100 nM thrombin. Non-specific binding of lysozyme to FAM-518 aptamer coupled beads was also observed (FIG. 3). The binding of lysozyme to FAM-518 aptamer was reversible upon addition of 0.5% SDS (FIG. 4).

What is claimed is:

1. A method for detecting an analyte in a sample comprising:

(a) contacting a sample with a fluorophore-labeled aptamer bound to a solid support, wherein the solid support is a bead;

(b) directly illuminating the aptamer with polarized light whereby the direct illumination of the fluorophore directly excites the fluorophore;

(c) measuring the fluorescence anisotropy of the fluorophore when said fluorophore-labeled aptamer is bound to said analyte; and (d) identifying the presence or amount of the analyte when the measured fluorescence anisotropy is greater than an anisotropy measurement obtained in the absence of bound analyte.

2. The method of claim 1 wherein the bead is a silica bead.

3. The method of claim 1 wherein the bead has a diameter between about 1 μm and about 10 μm.

4. The method of claim 3 wherein the bead has a diameter of about 5 μm.

5. The method of claim 1 wherein the bead is suspended in solution.

6. The method of claim 1 wherein the bead is arranged in a two-dimensional array.

7. The method of claim 1 wherein the aptamer comprises between about 10 and about 100 nucleotides.

8. The method of claim 1 wherein the aptamer is labeled with a fluorophore selected from the group consisting of fluorescein derivatives, eosin derivatives, coumarin derivatives, and rhodamine derivatives.

9. The method of claim 8 wherein the aptamer is labeled with carboxyfluorescein (FAM).

10. The method of claim 1 wherein the aptamer is part of an array of aptamers.

11. The method of claim 10 wherein the array comprises two or more addressable locations.

12. The method of claim 11 wherein each addressable location comprises a single type of aptamer.

13. The method of claim 11 wherein each addressable location comprises multiple types of aptamers.

14. The method of claim 13 wherein each type of aptamer is labeled with a fluorophore with unique spectral characteristics.

15. The method of claim 1 wherein the polarized light is laser light.

16. The method of claim 1 wherein the analyte is associated with a disease or disorder.

17. The method of claim 1 wherein the sample is obtained from a patient suspected of suffering from a disease or disorder.

18. The method of claim 1 wherein the analyte is a protein.

19. The method of claim 1 wherein the analyte is a metabolite.

20. The method of claim 1 wherein the sample is from a human patient and the analyte is associated with a disease or disorder.

* * * * *